(12) United States Patent
Uhlrich

(10) Patent No.: US 12,028,388 B2
(45) Date of Patent: Jul. 2, 2024

(54) PATIENT STATION FOR TELEMEDICINE

(71) Applicant: HOPI MEDICAL, Rosheim (FR)

(72) Inventor: Damien Uhlrich, Nancy (FR)

(73) Assignee: HOPI MEDICAL, Rosheim (FR)

( * ) Notice: Subject to any disclaimer, the term of this patent is extended or adjusted under 35 U.S.C. 154(b) by 125 days.

(21) Appl. No.: 17/825,104

(22) Filed: May 26, 2022

(65) Prior Publication Data
US 2022/0385707 A1 Dec. 1, 2022

(30) Foreign Application Priority Data

May 27, 2021 (EP) ..................................... 21305703

(51) Int. Cl.
| | |
|---|---|
| *H04L 65/403* | (2022.01) |
| *G16H 80/00* | (2018.01) |
| *H04N 5/262* | (2006.01) |
| *H04R 1/08* | (2006.01) |
| *G06F 3/0482* | (2013.01) |

(52) U.S. Cl.
CPC ........... *H04L 65/403* (2013.01); *G16H 80/00* (2018.01); *H04N 5/2628* (2013.01); *H04R 1/08* (2013.01); *G06F 3/0482* (2013.01)

(58) Field of Classification Search
CPC .... H04L 65/403; G16H 80/00; H04N 5/2628; H04R 1/08
See application file for complete search history.

(56) References Cited

U.S. PATENT DOCUMENTS

| | | | |
|---|---|---|---|
| 5,987,519 A | 11/1999 | Peifer et al. | |
| 2015/0035959 A1* | 2/2015 | Amble | A61B 5/0077 348/74 |

FOREIGN PATENT DOCUMENTS

FR 3050551 A1 10/2017

OTHER PUBLICATIONS

European Search Report issued in counterpart European Patent Application No. 21305703.7, dated Nov. 24, 2021 (7 pages).

* cited by examiner

*Primary Examiner* — Olisa Anwah
(74) *Attorney, Agent, or Firm* — Osha Bergman Watanabe & Burton LLP

(57) ABSTRACT

A patient station for telemedicine enabling transmission of patient data to a remote doctor station, via a telecommunication network includes a processing unit with an operating system, a main display device, and at least one first sensor of a first type generating first patient data. The processing unit is configured to generate a first video signal or a first image from the first patient data and display the first video signal or the first image on the main display device in a first display window, capture at least one display area of the first display window to generate a captured video signal, generate an output video signal comprising the captured video signal, emulate a digital-camera peripheral, wherein the output video signal is provided as output from the emulated digital camera peripheral to the operating system as digital camera-type peripheral device output, and provide the output video signal to the doctor station via the telecommunication network.

16 Claims, 6 Drawing Sheets

PATIENT STATION FOR TELEMEDICINE

TECHNICAL FIELD

The present disclosure relates to the general technical field of electronics and computing applied to medicine, and more particularly to telemedicine.

BACKGROUND

A consultation is the cornerstone of medical practice. It assumes that the two protagonists, the patient requiring care and the practitioner providing advice, prescriptions or care, are simultaneously present on one and the same site. In the present application, this practitioner is called a "doctor", without this involving any limitation with regard to his training, his qualifications or the nature of the care provided. The doctor typically provides a service resulting ideally in a diagnosis, a prognosis and a therapeutic proposition. This consultation may be supplemented, in the same appointment or later, by biological, imaging or other examinations providing additional information. The doctor may also request the enlightened opinion of expert colleagues, all aimed at underpinning and consolidating his diagnosis.

Remote consultation is the remote provision of this service when the patient and the doctor are not physically present in the same room, but are separate. For example, the two parties may be separated by a distance of a few meters when they are in two adjacent or nearby non-communicating rooms, up to distances of several thousand kilometers.

The primary aim of any medical consultation is to arrive at a diagnosis. Over his professional career, a doctor will perform around 200 000 consultations. Around 7 times out of 10, he manages to arrive at the diagnosis as early as the first meeting, which will be confirmed by other potential investigations and by evolution during treatment. In the other 30%, he will call upon external expertise in the form of additional examinations, opinions from specialist colleagues in the form of bilateral exchanges or large multidisciplinary consultative meetings. One or more hospital stays may prove necessary in the most complex cases.

Any medical consultation generally comprises the same steps, which may be broken down as follows: the doctor welcomes the patient, listens to him, asks him targeted questions that structure the diagnostic process, records his responses and observes his behavior and any salient facts.

After this initial purely conversational step, frequently, he makes the diagnosis that he will thereafter endeavor to confirm. He will assess the degree of repercussion of the illness on the individual, this being linked to the severity of the affliction, but also to the personality of the patient and his subjective feeling.

He then looks for objective elements accessible to the clinical examination in the medical office, for example by:
  precisely inspecting elements or areas indicated by the patient or discovered by the doctor,
  confirmatory palpation, revealing pain or inducing a muscular response, or exploratory palpation to find symptoms that are not perceived spontaneously by the patient,
  percussion, which is aimed at differentiating between solid areas, liquids and gaseous effusions,
  finally, auscultation, primarily cardiopulmonary, but also over the path of blood vessels, on the abdomen to find a breath, various noises or, by contrast, silence.

Remotely, the consultation, which becomes a remote consultation, requires the implementation of technical means so that the doctor is able to perform it in full. In general, remote consultation then consists in obtaining data relating to the patient, called "patient data", and in transmitting these data to the doctor. The patient data are collected on the site where the patient is located, called "patient site", using observation instruments and/or measuring instruments and computerized means, which form an assembly commonly called "patient station". These data are transmitted by the patient station to the workstation of the doctor located on a remote "doctor site", via a telecommunications network. The workstation of the doctor is equipped with computerized means and is commonly called "doctor station".

For the conversational phase, a device comprising videoconferencing software makes it possible to serve this purpose.

For the clinical examination, this involves using sensors capable of remotely transmitting the one or more signals that they generate so that the doctor is able to receive them and interpret them live. Sensors able to be connected to a processing unit close to the patient that transmits the signals is also one technical approach that works.

By way of example, still for the clinical examination, it is possible to mention the following connectable sensors for each of the four steps:
  a dermatoscope, an otoscope, a laryngoscope, an endoscope, an autonomous mobile camera, a retinograph, a slit lamp, etc. for the inspection step;
  using an echograph for the palpation step is possible by asking the assistant to move the probe onto the area to be examined. Besides the images that are produced, the doctor may in particular look at the patient's face, the reactions produced during the examination in order to detect a wince of pain, a look, a whimper, etc. It will be noted that, at this stage, a dual signal is required for the doctor: that from the echography probe and that from the video of the general scene so that said doctor is able to observe the reactions of the patient;
  the echograph for the percussion step as well finds an immediate response, since the doctor is able to differentiate between the black and homogeneous image of liquid, the heterogeneous appearance of solids and immediately stop the transmission of ultrasound using gases;
  The stethoscope for the auscultation step with possible processing of the sound signal in order to amplify or attenuate certain frequencies.

For more specialized examinations, reference may also be made for example to an electrocardiogram, an electroencephalogram, a Doppler echograph or a cardiac Doppler echograph.

Available platforms for telemedicine do not all have the same functional richness regarding, for example, the complexity of the remote clinical examination that it is possible to perform. Functional richness is linked primarily to the variety of different sensors able to be used with the platform. For some platforms comprising few functionalities and therefore compatible with few sensors, this often involves an industrial choice decided on by the software company, which consists in not developing or using electronic devices and sensors on the patient side. An examination requiring a certain type of sensor may therefore require the doctor to choose a particular platform. In addition, none of these platforms are interoperable, meaning that a doctor who has subscribed to one platform cannot perform a remote consultation for a patient who has subscribed to a different platform.

In most cases, the platforms offer at least one videoconferencing function for performing the conversational phase of the remote consultation. This videoconferencing function (provided by a software that is independent and autonomous or integrated into a Web browser) allows at best the simultaneous transmission of a video signal and an audio signal.

The inventors have recognized that during a remote consultation, it may be necessary to use various sensors producing data of various types that are not all able to be transmitted through videoconferencing. Furthermore, it may be necessary to transmit multiple signals simultaneously, for example one signal corresponding to an electrocardiogram, and another corresponding to an image of the patient captured by a webcam, this not being possible using a conventional videoconferencing platform.

In addition, some sensors are provided by a manufacturer with imposed software that makes it possible to display the data arising from the sensor in a dedicated graphical interface, but do not allow the data to be accessed in order to transmit them via a videoconferencing platform. Thus, in some cases, the data arising from the sensor are displayed on the patient station but cannot be transferred to the doctor station. In other cases, the transfer is possible but requires the use of a particular platform that is not interoperable with other platforms.

More generally, the "lack of interoperability" of the platforms causes, inter alia, the following problems:

Segmentation of the medical offering for the patient. Depending on the platform to which he has subscribed or to which he has access, he might not be able to access his chosen doctor. This is all the more true if said patient lives in care home that has chosen a single remote consultation solution.

Segmentation of the patients for the doctor. The doctor might not be able to respond to all his patients. If he subscribes to multiple platforms, he might not be able to provide medical services of equivalent quality, since these depend on the functional richness of each of said platforms.

Thus, embodiments of the present disclosure are intended to at least partially overcome some of the abovementioned problems. In particular, embodiments of the present disclosure intend to propose a patient station compatible with the majority of consultation platforms able to be used in a doctor station.

GENERAL DISCLOSURE

According to a first aspect, embodiments of the present disclosure relate to a patient station enabling transmission of patient data to a remote doctor station, via a telecommunication network, the patient station comprising:
a processing unit;
a main display device; and
at least one first sensor of a first type generating first patient data.
The processing unit is configured to:
generate a first video signal or a first image from the first patient data and display the first video signal or the first image on the main display device in a first display window;
capture at least one display area of the first display window to generate a captured video signal;
generate an output video signal comprising the captured video signal;
emulate a digital camera peripheral, wherein the output video signal is provided as output from the emulated digital camera peripheral; and
provide the output video signal to the doctor station via the telecommunication network.

Such a configuration makes it possible to send, to the doctor station, an output video signal representative of patient data arising from all types of sensors, including a sensor whose data are able to be displayed, in the form of an image or video, only in a graphical interface dedicated to the sensor. In particular, it is possible to select, by way of the capture function, also called screen capture, a display area in the first display window in order to extract all or part of the first video signal or the first image and transmit same to the remote doctor station, and to do so regardless of the software and the interface imposed by the manufacturer of the sensor for displaying the first video signal or the first image. Such a configuration therefore makes it possible to use a wide variety of sensors during a remote consultation.

Furthermore, such a patient station makes it possible to transmit patient data to any remote doctor station provided that this doctor station is configured to receive a video signal. In particular, this patient station is compatible with any doctor station equipped with remote consultation software provided with a videoconferencing function or with "simple" videoconferencing software. The patient station is therefore compatible with almost all, if not all, existing doctor stations.

The patient station according to embodiments of the disclosure therefore makes it possible to transmit a wide variety of patient data arising from various types of sensors to almost all doctor stations. In other words, by virtue of the patient station, a doctor has the ability to perform a complex clinical examination based on various patient data, regardless of the remote consultation software that he uses, or even using "simple" videoconferencing software that the majority of patients and doctors may have available.

It should be noted that the output video signal may comprise only the captured video signal, in which case these two signals are identical, or may comprise one or more other signals in addition to the captured video signal.

In some embodiments, the patient station furthermore comprises at least one second sensor of a second type, different from the first type, generating second patient data, and the processing unit is configured to:
generate a second video signal from the second patient data; and
generate the output video signal by combining the second video signal and the captured video signal.

Such a configuration allows the simultaneous use of multiple sensors during the remote consultation and simultaneous transmission of the video signals arising therefrom to the doctor station.

In particular, combining the second video signal and the captured video signal to form a single combined video signal makes it possible to use conventional videoconferencing software that allows the transmission of just a single video signal (and a single audio signal).

In some embodiments, the processing unit comprises an operating system and the output video signal is identified by the operating system as a video signal coming from the emulated (also known as "virtual") digital camera peripheral. In other words, a hardware device identifier (or ID) and a format of the output video signal are identical to those of a digital camera peripheral such as a digital camera connected to the processing unit via, for example, a universal serial bus (USB) or Thunderbolt™ interface. The terms "peripheral" and "peripheral device" are used interchangeably throughout this disclosure.

Such a configuration makes it possible to recognize a signal coming from the capture of a display area as a "typical" video signal originating from a physical digital camera. This functionality may be achieved by way of an emulator that mimics the signature and response of a physical (i.e., "real") digital camera when queried by the operating system, resulting in an output video signal that appears to the operating system as though it originates from a physical digital camera.

Digital-camera peripheral devices may include, for example, a USB connected webcam, and may have particular device identifiers recognized by the operating system as digital camera identifiers. Thus, according to some embodiments, the peripheral device exists as an instantiation of a code-based object, but does not physically exist (i.e., this peripheral is "virtual"). The output video signal will thus be referenced by the operating system and thereby by a software executed by the processing unit among the video signals coming from digital cameras connected to the processing unit.

The emulator may be, for example, a software component commonly referred to as a "virtual driver". Such a software component, when operated by the processing unit, emulates the digital camera peripheral and provides access information to the operating system for accessing the output video signal (as output signal from the emulated peripheral).

In some embodiments, the output video signal is provided to the doctor station by way of videoconferencing software. The processing unit is then configured to provide the output video signal to the videoconferencing software as output signal from the emulated digital camera peripheral. The output video signal is thus referenced by the videoconferencing software as available video signal, as would be a video signal coming from a digital camera in communication with the processing unit.

Such a configuration makes it possible to choose the output video signal (coming from the capture of a display area) as signal used by the videoconferencing software for transmission to the network. In practice, the output video signal may be selected by the user of the patient station from the scrolling menu on the interface of the videoconferencing software, which lists the available video signals.

In some embodiments, the patient station comprises an audio sensor connected to the processing unit and generating a first audio signal, and the processing unit is configured to:
  generate an output audio signal comprising the first audio signal;
  emulate a microphone peripheral, wherein the output audio signal is provided as output from the microphone peripheral; and
  provide the output audio signal to the doctor station via the telecommunication network.

It is thus possible to recognize a first audio signal coming from a particular audio sensor, such as for example a stethoscope, as a "typical" audio signal originating from conventional audio hardware. The first audio signal is thus referenced by the operating system and, thereby, by the software executed by the processing unit, among the audio signals coming from the microphones connected (e.g., via USB) to the processing unit.

This functionality may be achieved by way of emulator software that mimics the signature and response of a physical microphone when queried by the operating system, resulting in an audio signal that appears to the operating system as though it originates from a physical microphone connected to the processing unit.

In particular, in some embodiments, the output audio signal is transmitted to the doctor station by way of videoconferencing software. The processing unit is then configured to provide the output audio signal to the videoconferencing software, as output from the emulated microphone peripheral.

Such a configuration makes it possible to choose the first audio signal as signal used by the videoconferencing software and transmitted to the network by executing this software. In practice, the first audio signal may be selected by the user of the patient station from the scrolling menu on the interface of the videoconferencing software, which lists the available audio signals.

In some embodiments, the processing unit is configured to display the first display window within a second display window of a graphical control interface.

Such a configuration makes it possible in particular to control the position and/or the size of the first display window comprising the first video signal arising from the first sensor by controlling the position and/or the size of the second display window.

In some embodiments, the processing unit is configured so as to automatically redimension the first display window displayed in the graphical control interface.

Such a configuration makes it possible, when a third display window comprising a video signal or an image arising from another sensor is displayed in the second display window, to redimension the first display window in order to simultaneously display the entire first display window and the entire third display window within the second display window.

In particular, this makes it possible, when displaying (on the display device of the patient station) a video signal coming from a webcam of the doctor station and allowing the patient to see the doctor, and when displaying a video signal (or an image) arising from a sensor measuring and generating patient data, to redimension the first window displaying the video signal of the sensor with respect to the window displaying the video signal of the doctor. It is thus possible to see the doctor while at the same time capturing a display area of the first window.

In some embodiments, the first display window forms part of a graphical interface dedicated to the first sensor. This is in particular the case when the first sensor originates from a manufacturer imposing software for displaying the data arising from the sensor in a dedicated graphical interface. Typically, besides the first display window, the graphical interface comprises menus, icons, etc. dedicated to the control of the first sensor.

In some embodiments, the processing unit comprises a main unit and an auxiliary unit, the auxiliary unit being configured so as to generate the first video signal or the first image from the first patient data and display the first video signal or the first image on an auxiliary display device; and the main unit being configured so as to duplicate the display of the first video signal or the first image on the main display device in the first display window.

Such a configuration makes it possible to use an auxiliary unit to generate the first video signal (or the first image), which is separate from the main unit, the main unit being configured and used to transmit the output video signal to the doctor station.

In particular, it is possible to perform a remote consultation comprising the use of a sensor requiring a particular auxiliary unit that is not the main unit. This is particularly advantageous when a sensor requires the use of an electronic tablet or a multifunction telephone (or smartphone), forming the auxiliary unit, while the videoconferencing application used to transmit the video signals is executed on a personal computer (or PC) forming the main unit.

In some embodiments, generating the output video signal comprises a step of filtering and/or redimensioning the captured video signal and/or the second video signal.

Such a configuration makes it possible to modify parameters of the captured video signal and/or of the second video signal before combining them to generate the output video signal. In particular, this makes it possible to modify the resolution and/or the dimensions of the captured video signal and of the second video signal to form a common resolution (and/or common dimensions) in order to generate an output video signal having homogeneous parameters.

In some embodiments, the first sensor is a camera (for example a hand-held camera, a dermatoscope camera, a slit lamp camera, a laryngoscope camera, etc.), an echograph, an electrocardiograph, an electroencephalograph, a spirometer, a tensiometer, a thermometer, an oximeter, a scales, a refractor, a tonometer, a pachymeter, a frontofocometer, a keratometer, an autorefractometer or a radiology apparatus such as a scanner, a magnetic resonance imaging (MRI) apparatus or a position emission tomography (or PET scan) apparatus, this radiology apparatus possibly being coupled to a picture archiving and communication system or "PACS".

Embodiments of the present disclosure also relate to a system comprising the abovementioned patient station and a doctor station, the doctor station comprising a processing unit configured to receive the output video signal transmitted by the patient station.

According to a second aspect, embodiments of the present disclosure relate to a method for transmitting patient data to a remote doctor station via a telecommunications network, the method comprising the following steps:
generating a first video signal or a first image from first patient data arising from a first sensor of a first type and displaying the first video signal or the first image on a main display device in a first display window;
capturing at least one display area of the first display window in order to generate a captured video signal;
generating an output video signal comprising the captured video signal;
emulating a digital camera peripheral, wherein the output video signal is provided as output from the emulated digital camera peripheral;
transmitting the output video signal to the doctor station via the telecommunication network.

In some modes of implementation, the method further comprises:
generating a second video signal from second patient data arising from a second sensor of a second type; and
generating the output video signal by combining the second video signal and the captured video signal.

The abovementioned features and advantages, along with others, will become apparent upon reading the following detailed description of exemplary embodiments of the proposed patient station and method. This detailed description refers to the appended drawings.

BRIEF DESCRIPTION OF THE DRAWINGS

The appended drawings are schematic. They are intended primarily to illustrate the principles of the disclosure.

In these drawings, elements (or parts of element) that are identical or analogous are referenced using the same reference signs from one figure (FIG) to another.

DETAILED DESCRIPTION

Figure 1:
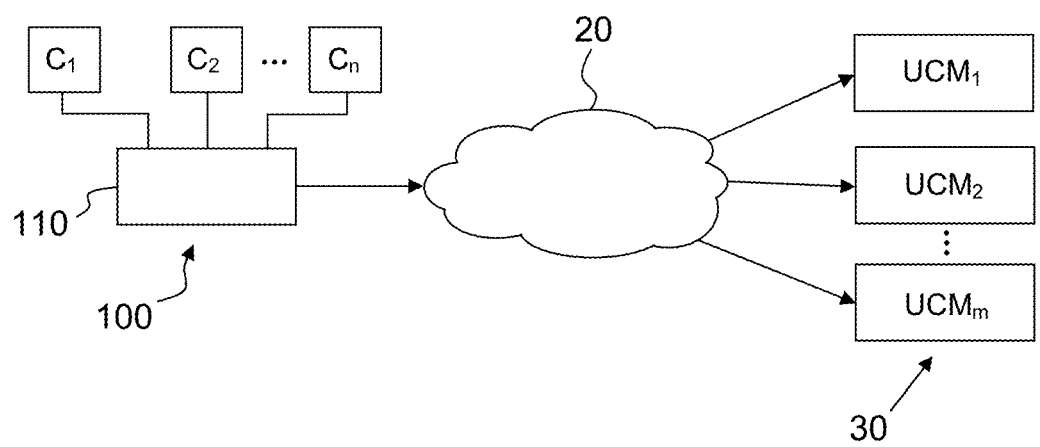
FIG. 1 is a general diagram showing one example of a remote consultation system.

FIG. 1 illustrates a remote consultation system in which patient data collected by a patient station 100 on a patient site are transmitted, via a telecommunication network 20, to one or more remote doctor sites 30. The patient station 100 comprises a processing unit 110 to which a set of sensors C1, C2, . . . Cn of various types are connected. The processing unit 110 is generally a computer, such as, for example, a desktop personal computer, a laptop computer, a tablet or a smartphone. The sensors C1 to Cn may for example comprise image sensors or audio sensors that may be used to allow the patient to be seen, listened to or examined. According to the present description, an image sensor is understood to mean a sensor that produces data capable of generating signals of various types, such as videos, photos, images, animated images, alphanumeric data or graphical data. According to the present description, an audio sensor is a sensor that produces data in an audio format. By way of example, the image sensors may be a webcam, a hand-held camera, a dermatoscope camera, a slit lamp camera, a laryngoscope camera, any kind of digital camera, an echograph, an electrocardiograph, an electroencephalograph, a spirometer, a tensiometer, a thermometer, an oximeter, a scales, a refractor, a tonometer, a pachymeter, a frontofocometer, a keratometer, an autorefractometer and/or a radiology apparatus. By way of example, the audio sensors may be a microphone and/or a stethoscope.

The processing unit 110 is connected to a telecommunication network 20, for example the Internet, and is therefore able to transmit and receive flows of information, in particular video and audio signals, during videoconferencing sessions with processing units UCM1 to UCMm, hereinafter called "doctor processing unit", located on one or more doctor sites 30 used by doctors and also connected to the telecommunication network 20, such as the Internet. The processing units may connect to the Internet using various means: Ethernet, Wi-Fi, 3G/4G/5G modem, satellite modem, etc.

Although the remote consultation is generally performed from a patient site to one doctor site 30 comprising a doctor processing unit UCM1, it is also possible to transmit the patient data from the patient site to a plurality of doctor sites 30, the doctor sites comprising respective doctor processing units UCM1 to UCMm.

FIGS. 2A to 2D show some examples of patient stations 100. These patient stations are installed at the site where the patient may be located, such as for example in a remote consultation studio, in a pharmacy, in a medico-social establishment, in a hospital, in a doctor's office, where the patient works or lives, etc.

Figure 2A:
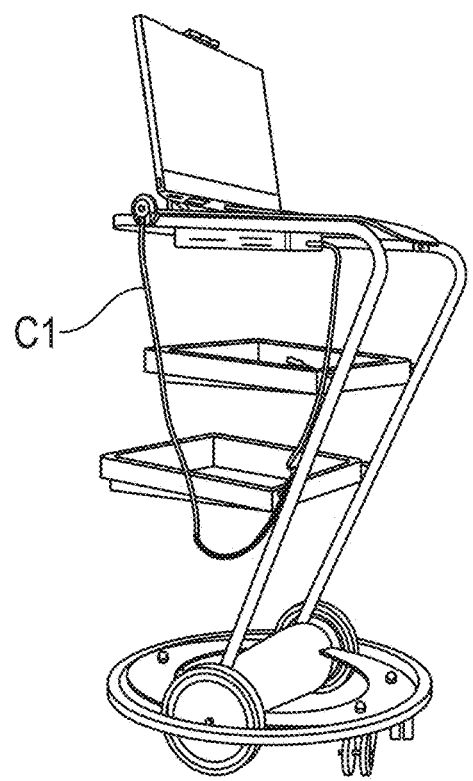
FIGS. 2A to 2D show examples of patient stations able to be used on the patient site during a remote consultation.

FIG. 2A is one example of a patient station 100 of remote consultation trolley type. It comprises a personal computer with an orientable touch screen, a webcam, a microphone and speaker system, a keypad, a touch pad, an identification card reader (for identifying the patient and/or the user of the patient station), a set of sensors, all supported by a metal structure mounted on wheels with a support panel for the computer and storage racks for the sensors. A stethoscope sensor C1 may be seen in FIG. 2A.

Figure 2B:
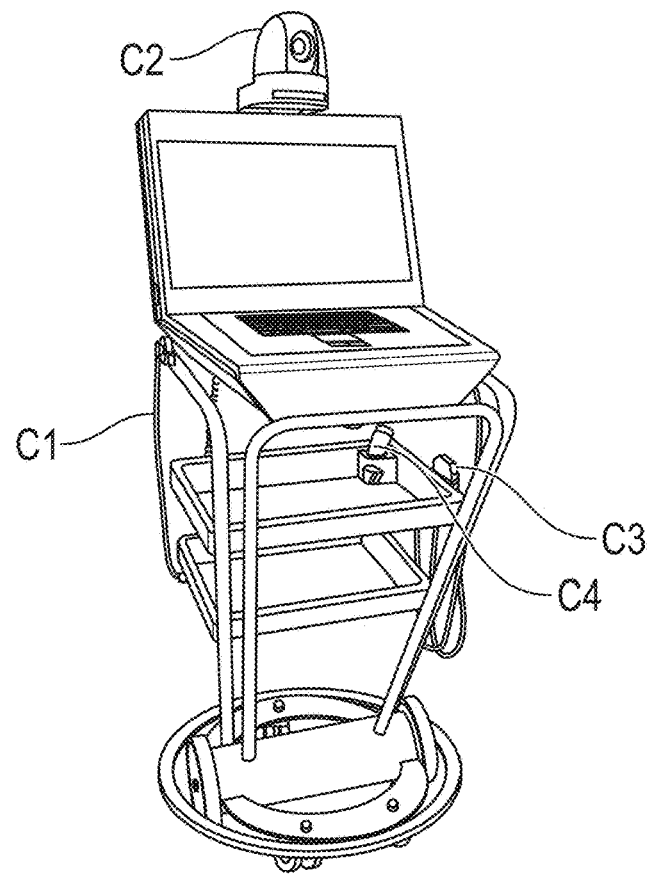

FIG. 2B is one example of a patient station 100 of remote consultation trolley type. It comprises a computer with an orientable touch screen, an orientable camera (also called PTZ camera, PTZ being the acronym for "pan tilt zoom"), a microphone and speaker system, a capacitive keypad positioned underneath a glass panel, a system for disinfecting the hands by spraying a hydro-alcoholic solution, a power supply battery, an electrical recharging system with a magnetic connection, an identification card reader, all supported by a metal structure mounted on wheels with a support panel for the computer and storage racks for the sensors. In the example of FIG. 2B, it is possible to see a stethoscope sensor C1, a sensor C2 formed by the orientable camera, an echograph sensor C3 and an otoscope sensor C4.

Figure 2C:
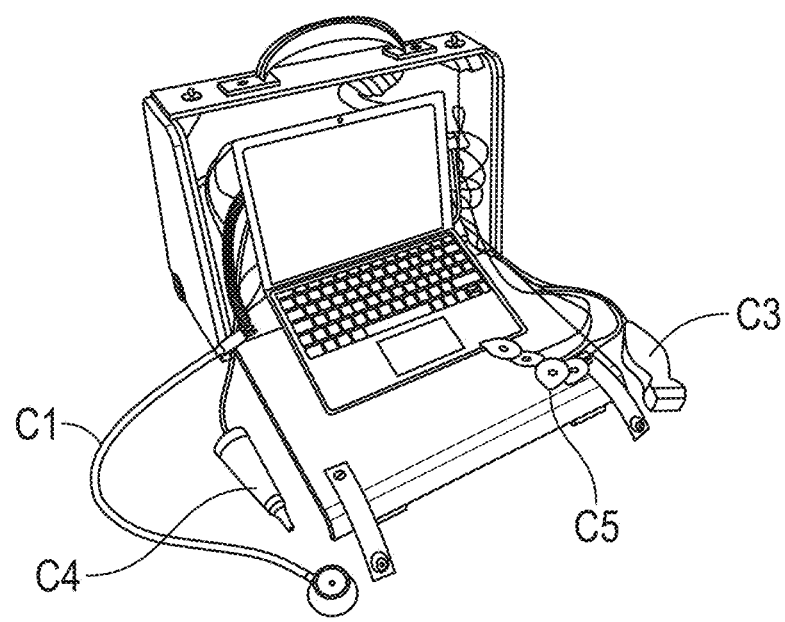

FIG. 2C is one example of a patient station 100 of remote consultation briefcase type. It comprises a computer with an orientable touch screen, of "tablet computer" type, a webcam, a microphone and speaker system, a keypad, a touch pad, a power supply battery, an electrical recharging system with a magnetic connection, an identification card reader, all supported by a plastic structure with compartments for storing the sensors. In the example of FIG. 2C, it is possible to see a stethoscope sensor C1, an echograph sensor C3, an otoscope sensor C4 and an electrocardiograph electrode sensor C5.

Figure 2D:
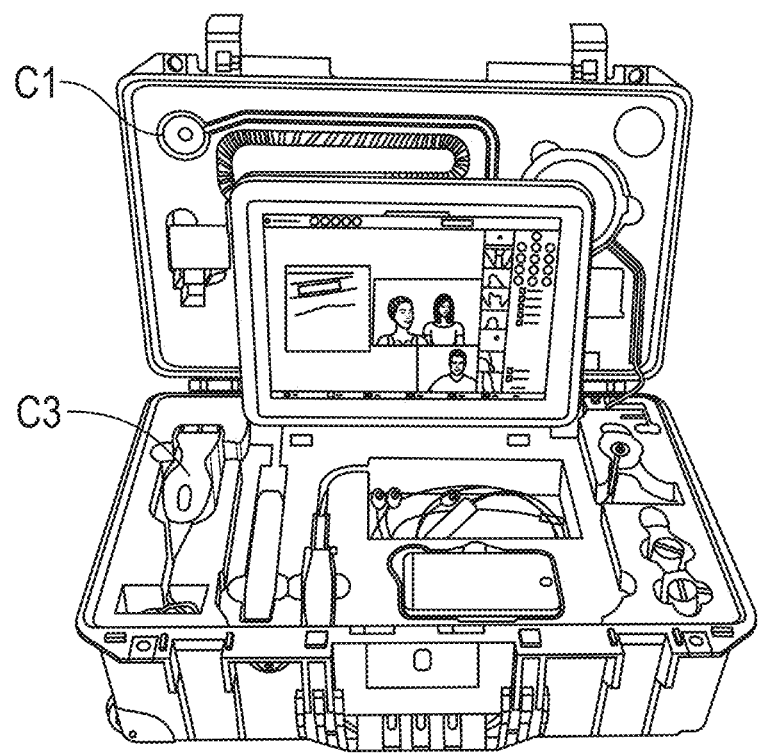

FIG. 2D is one example of a patient station 100 of remote consultation briefcase type. It comprises a computer with an orientable touch screen, of "tablet computer" type, strengthened for a rigorous environment, a webcam, a microphone and speaker system, a keypad, a touch pad, a power supply battery, an electrical recharging system with a magnetic connection, an identification card reader, all supported by a plastic structure complying with multiple standards ("Stanag" standard and "IP67" protection index) with an internal receptacle made of foam for storing the sensors. In the example of FIG. 2D, it is possible in particular to see a stethoscope sensor C1 and an echograph sensor C3.

Other possible types of patient station 100, not shown, may comprise tablet and smartphone devices.

Figure 3:
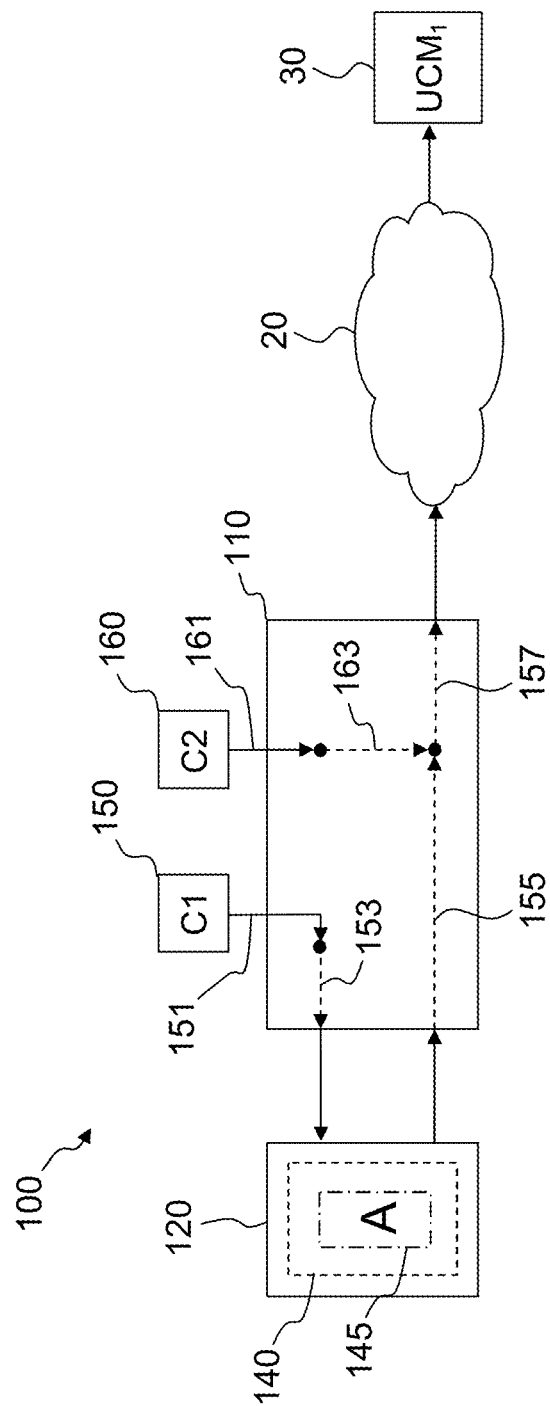
FIG. 3 is a diagram of one example of a patient station.

FIG. 3 is a diagram of a remote consultation system comprising one example of a patient station 100 according to embodiments of the present disclosure. The patient station 100 comprises a first sensor 150 of a first type providing first patient data 151, a second sensor 160 of a second type providing second patient data 161, a processing unit 110 that receives the first and second patient data 151, 161, and a display device 120. The sensors 150, 160 are connected to the processing unit by a wired link (for example a USB cable) or a wireless link (for example a link using radio waves, such as a "Bluetooth" link).

The processing unit 110 is generally equipped with an operating system facilitating execution of software, in particular remote consultation software, videoconferencing software, and software dedicated to sensors for displaying video signals (or images) provided by sensors in display windows, in particular within graphical interfaces.

According to the example shown in FIG. 3, the processing unit 110 is configured so as to generate a first video signal 153 or a first image from the first patient data 151 coming from the first sensor 150. The first video signal 153 is displayed in a first display window 140 dedicated to the sensor 150. Software with a screen capture function, commonly called "SCR" in line with the acronym for "screen capture recorder", is executed by the processing unit 110 in order to record part of the first video signal 153 displayed in the first window 140. The screen capture software makes it possible to capture a display area 145 of the first display window 140 in which the displayed video signal 153 will be recorded. For this purpose, it is possible to choose multiple parameters, such as the size and/or the position of the display area 145 to be captured. The screen capture function thus makes it possible to obtain a captured video signal 155 from the first video signal 153 arising from the first patient data 151 coming from the first sensor 150.

This configuration with the screen capture function is particularly advantageous when the video signal 153 cannot be transmitted directly to the network 20 by the processing unit 110 and is only able to be displayed on the display device 120 in a first display window 140 linked to the software dedicated to the first sensor 150, often provided by the manufacturer of the sensor. Such a sensor may in particular be a video surveillance camera (commonly called "IP camera"), an otoscope, an echograph or an electrocardiograph.

In the example of FIG. 3, the display area 145 to be captured is contained within the first display window 140, but it is possible to choose a display area 145 to be captured of the same size as the display window 140, or even of a size larger than the display window 140.

In some variants, the screen capture function makes it possible to obtain a captured video signal 155 from a first image arising from patient data coming from the first sensor 150. The first image is first of all displayed in the first display window 140, and it is then captured in order to generate the captured video signal 155. The screen capture function thus makes it possible to transform an image arising from a sensor into a video signal through video recording of this image. According to other variants, it is possible to use the screen capture function of the patient station 100 to transform a photograph, alphanumeric data or graphical data into an output video signal 153. This proves to be useful for sensors able to provide images and/or graphics, such as echographs and electrocardiographs.

Generating the captured video signal 155 may also comprise a step of filtering, for example a resampling or a redimensioning, in order to define a format of the captured video signal 155. In particular, it is possible to trim certain areas of the signal (suppress vertical or horizontal bands in the video for example). In the present description, a video signal format comprises in particular the resolution of the signal (generally expressed in pixels by pixels), the digital encoding (for example RGB 24 bits) and the video frame rate (generally expressed in number of images per second).

The captured video signal 155 is then transmitted as output video signal 157 to the network 20 using videoconferencing software. The software that is used may also be remote consultation software with a videoconferencing function. For this purpose, the processing unit 110 may instantiate an emulator configured to emulate functionality associated with a digital camera peripheral and resulting in creation of an emulated peripheral.

The emulator may be embodied as code executed by the processing unit 110 and configured to present an identifier consistent with identifiers associated with digital camera peripherals (e.g., webcams). The emulator may enable the output video signal 157 to mimic and be recognized as a "typical" video signal (e.g., as originating from a conventional video source) capable of being transmitted to the network in the same way as a video signal arising from a digital camera would be. In other words, a virtual digital camera, also referred to as a virtual peripheral, is created by the emulator. In practice, the virtual peripheral presents an interface to the operating system consistent with that of a digital camera (e.g., a webcam), and the operating system therefore interprets the output video signal 157 as coming from a digital camera, even though, in reality, such a digital camera does not physically exist and is not connected to the processing unit 110.

In general, the output video signal 157 corresponding to the screen capture may then be selected by the user from a scrolling menu on the graphical interface of the videoconferencing software that makes it possible to select video signals, just as the signal coming from a webcam connected to the processing unit 110 would be.

In some cases, the videoconferencing software may apply a processing operation to the output video signal 157 before transmitting it to the doctor station 30 via the network 20 in order to modify the format of the output video signal 157. The kind of processing operations that are applied may for example be video compression (in particular compression of the type H264, Mpeg2, Mpeg4, H263, VP8, VP9), a resolution change, a precision change, or packetization of the signal in order to facilitate the transportation of the signals through an Internet protocol used by the network.

According to other examples, as illustrated in FIG. 3, it is possible to combine the captured video signal 155 with a second video signal 163 arising from second patient data 161 coming from a second sensor 160. This is useful in particular when the second sensor 160 is a webcam and it is desired to combine the signal coming from this webcam and a signal coming from the capture of a window displaying the signal from the first sensor 150. It may be conceived, for example, to combine a signal coming from a webcam and a signal coming from an echograph requiring the use of dedicated software.

The combination may be performed in various ways. In particular, it is possible to produce an output video signal 157 that is a signal that is spatially combined using a video mixer. Such a signal corresponds, once it is displayed on a display device, to a video comprising multiple juxtaposed parts. The combination then makes it possible to obtain a single output video signal 157 that is able to be transmitted and received using conventional videoconferencing software.

In the example of FIG. 3, only two sensors 150, 160 are connected to the patient station 100, but it is possible to have a larger number of sensors connected to the patient station 100. In this case, it is possible to combine more than two signals arising from data coming from these sensors using the abovementioned combination method.

According to some embodiments, the sensors comprise audio sensors the data from which may be processed by the processing unit 110 in order to generate audio signals, for example sensors such as a stethoscope or a microphone (a micro-headset able to be connected to the patient station using a 3.5 mm jack connector also falls under this type of sensor). In the same way as for the video signals, it is possible to combine multiple different audio signals to form a single output audio signal by way of the processing unit 110. The audio signals may be combined using an audio mixer. It is additionally possible to apply filtering operations to one or more audio signals before performing the combination, in particular a frequency equalization filtering operation (in particular using a filter commonly called an "equalizer") in order to amplify or attenuate certain sound frequency bands.

Similar to the output video signal 157, a microphone emulator may be instantiated to emulate functionality associated with a microphone peripheral. The emulator may be embodied as code executed by the processing unit 110 and configured to present an identifier consistent with identifiers associated with microphone peripherals (e.g., a built-in webcam microphone). The emulator may enable the output video signal to mimic and be recognized by the operating system as an audio signal coming from a conventional microphone-type peripheral. This then makes it possible to select the output audio signal as audio signal that will be used by the videoconferencing software for the transmission to the network. The selection may in practice be made using the scrolling menu on the graphical interface of the videoconferencing software, making it possible to select the audio signals.

Figure 4:
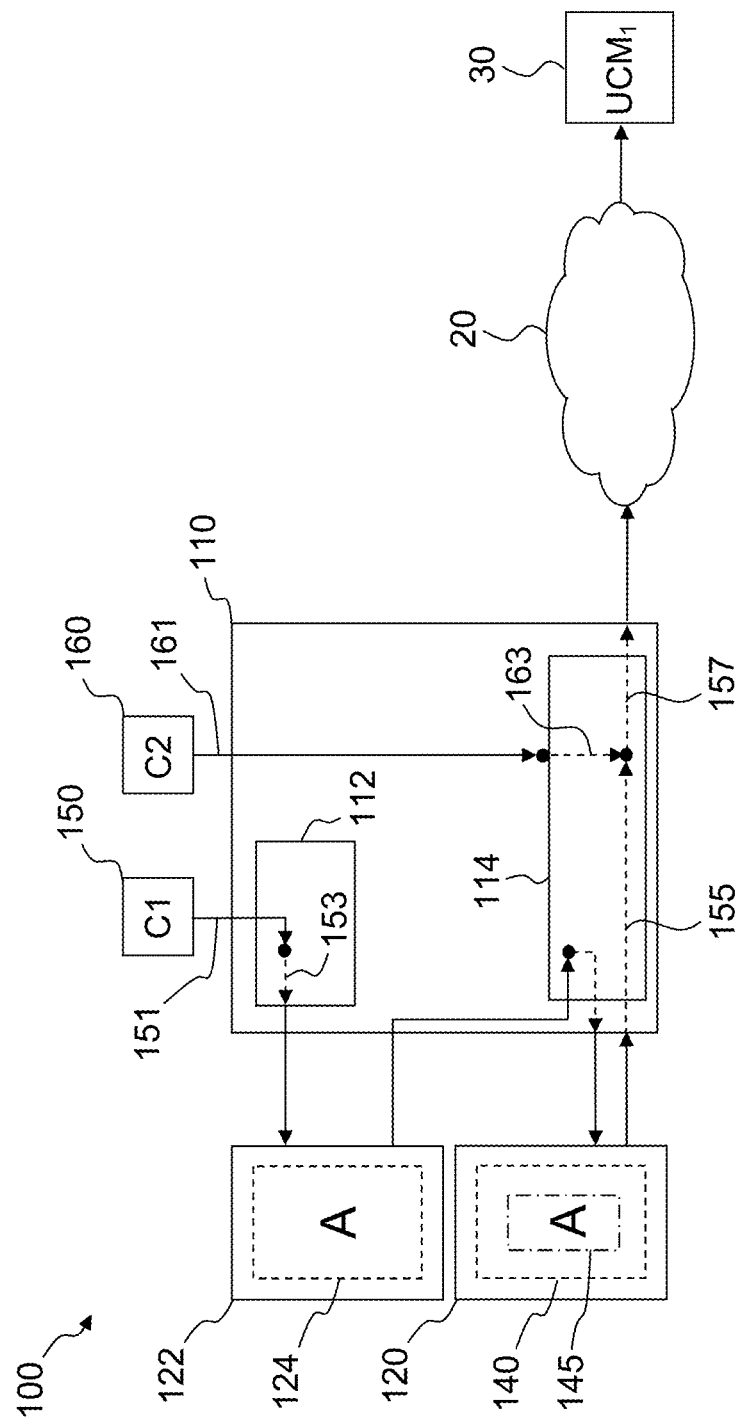
FIG. 4 is a diagram of another example of a patient station in which the processing unit comprises a main unit and an auxiliary unit.

FIG. 4 illustrates another example of a patient station 100 in which the processing unit 110 comprises two separate units: an auxiliary unit 112 and a main unit 114.

The auxiliary unit 112 is used in particular to generate the first video signal 153 or the first image, while the main unit 114 is used in particular for the videoconferencing function.

The auxiliary unit 112 is configured so as to display the first video signal 153 arising from the first patient data 151 coming from the first sensor 150 on an auxiliary display device 122 in a display window 124, also called auxiliary display window.

The operating system of the main unit 114 is furthermore configured so as to execute screen mirroring software aimed at duplicating the auxiliary display window 124 on the main display device 120. The first video signal 153 is thus displayed in a display window 140 of the main display device 120, and a display area 145 of the window 140 may then be captured by the system described above in order to generate a captured video signal 155. In this example, it is also possible to combine the captured video signal 155 with a second video signal 163 arising from second patient data 161 coming from a second sensor 160 by way of the main unit 114.

The screen mirroring software is able to duplicate the display 124 by exchanging data between the auxiliary unit 112 and the main unit 114 using various means and, for example, via a Wi-Fi communication network to which the auxiliary unit 112 and the main unit 114 are connected. The video signal arising from duplication is generally displayed on the main display device 120 by way of dedicated software.

This configuration makes it possible to use the patient station 100 with sensors provided with dedicated software that is compatible with the operating system used in the auxiliary unit 112 but is not compatible with the operating system used in the main unit 114. A multifunction telephone (or smartphone) camera for example falls into this category. Specifically, the integrated camera of the smartphone is compatible with the operating system of the telephone (which is considered to be an auxiliary unit), but the integrated camera of the telephone is not recognized as a camera or webcam by the operating system of the main unit 114. A surveillance camera or any other type of sensor for which the video that is produced is able to be displayed only via software executed on a telephone or another similar device also falls into this category.

Figure 5A:
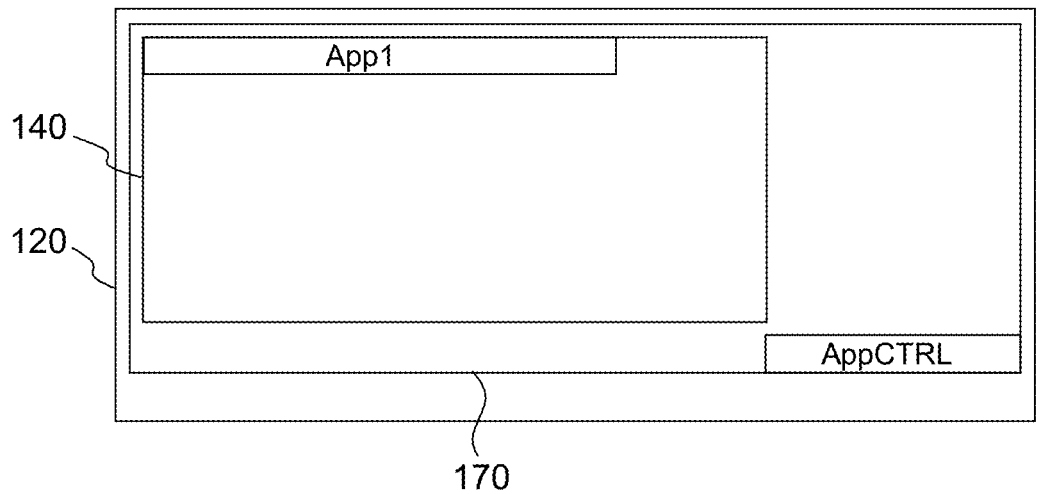
FIGS. 5A to 5B illustrate various examples of the display of video signals on the display device of the patient station.
Figure 5B:
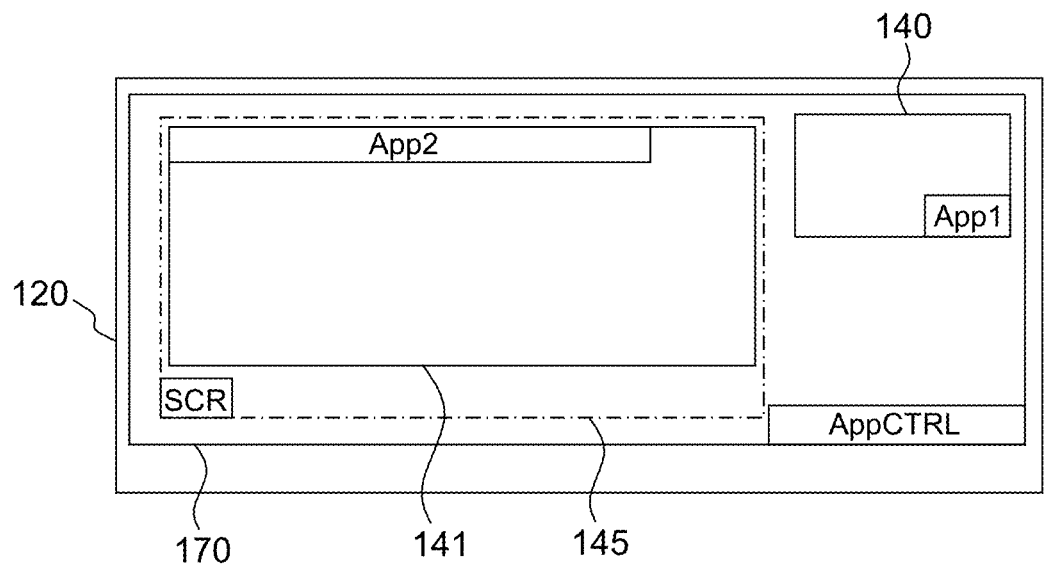

FIGS. 5A and 5B illustrate the display on the display device 120 of the patient station 100 during a remote consultation according to multiple usage examples.

According to one example, remote consultation software AppCTRL is executed on the patient station 100 in order to implement a remote consultation. The remote consultation software is executed by the processing unit 110 and generally has a graphical control interface 170 that is displayed on the display device 120.

A user of the patient station 100, who may be a consultation assistant or the patient himself, is able to interact with the remote consultation software via his graphical control interface 170 using peripheral devices conventionally connected to the processing unit 110, such as a mouse, a keypad, a touch screen or a touch pad.

The user of the patient station 100 may then activate a sensor by launching dedicated software App1, that is to say he may for example use a webcam by launching the visualization software dedicated to the webcam. It is also possible to activate multiple sensors by way of multiple dedicated pieces of software. One or more sensors may also be activated automatically when the operating system of the processing unit 110 is booted.

According to the example illustrated in FIG. 5A, the processing unit 110 may ensure that the display window 140 containing the video signals or images coming from the sensor (for example from the webcam) is displayed within the graphical control interface 170. It is thus possible to control the first display window 140 by way of the graphical control interface 170. In particular, if the window of the graphical control interface 170 is reduced in size via an intentional action by the user (for example with the mouse connected to the processing unit 110), then the window 140 of the dedicated software App1 that is integrated within the graphical control interface 170 will also have its size reduced proportionally.

The displaying of the display window 140 of software App1 within the graphical control interface 170, which may be seen as "taking control" of the display window 140 of the software App1 dedicated to the sensor by the remote consultation software AppCTRL, may be performed by various means. In particular, it is possible to program the remote consultation platform in a "C++Qt" development environment and to use control-taking functions known as "QWindow::fromWinId" and "QWidget::createWindowContainer".

Moreover, if the software App1 dedicated to the sensor is of the kind executed within a Web browser, that is to say the display window of the software App1 is displayed within the display window of the Web browser, then the remote consultation software AppCTRL will take control of the Web browser within which the software App1 is executed. This is made possible for example by using the "C++ Qt" development environment, which makes it possible to implement a Web browser in different software by way of a rendering engine, also generically called a "Web engine", and more specifically called "Webkit" or QTWebengine" in the case of a "C++QT" development environment.

In practice, if the software App1 dedicated to the sensor is of the kind executed within a Web browser, the remote consultation software AppCTRL injects the Web address of the software App1 into the Web browser (which is integrated into AppCTRL by way of the rendering engine), and AppCTRL then displays the display window of the Web browser in its graphical interface 170.

According to one variant illustrated in FIG. 5B, when a user launches second software App2 dedicated to a second sensor while first software App1 dedicated to a first sensor is already being used, then the processing unit 110 automatically redimensions the first display window 140 (of the software App1) in order to display the new display window 141 (of the software App2) in full. It does this so that the two windows 140, 141 are simultaneously visible within the graphical control interface 170 on the display device 120. This variant is particularly advantageous when the user wishes to visualize video signals from two sensors simultaneously.

Moreover, it is then possible to execute screen capture software SCR in order to capture a display area 145 of the display window 141 of the software App2. This variant is particularly advantageous when the user wishes to visualize video signals arising from two sensors simultaneously and one of the sensors requires the use of a screen capture function to transmit data to the network.

For example, it is thus possible, on the display device 120, to visualize the doctor image coming from a webcam displayed in a first window 140, while at the same time capturing a display area 145 of the window 141 of the software App2.

Although, in the example of FIG. 5B, the captured display area 145 encompasses the display window 141 of the software App2, according to other examples, it is possible for the captured display area 145 to cover only part of the display window 141.

According to some embodiments, it is possible to define and save user profiles in a storage memory of the processing unit 110. These profiles form a set of instructions for activating a certain number of sensors and their respective dedicated software, for defining the format of the video signals generated by the processing unit 110, for scheduling or not scheduling the launching of one or more pieces of screen capture software (and for defining the size and position of the display areas to be captured), or else for defining the kind of filtering operations to be applied to the video and/or audio signals arising from the various sensors.

When the clinical examination to be performed during a remote consultation is of a certain type, for example an examination of the ear canals, then the user may select an appropriate profile that will activate the sensors needed for the examination, for example a webcam and an otoscope.

Furthermore, the profiles may serve to define the parameters regarding the automatic redimensioning of certain display windows 141 within the graphical control interface 170 when multiple sensors are used simultaneously.

Finally, a default profile may be defined, for example a basic profile for simply performing a videoconference. The default profile will be applied at the initial launching of the processing unit 110. Other profiles defined beforehand may be applied during a remote consultation session by the user of the patient station 100, for example by clicking a mouse or else via a possible touch function of the display device 120.

The profiles may also serve to define the video and/or audio format to be used for the output video signal and/or the output audio signal. The profiles may be stored in the memory of the processing unit in the form of a file (for example a file in .xml or .json format) or else in a database accessible via a network. Advantageously, as long as two different profiles define the same output video signal format and the same output audio signal format, it is possible to switch from one to the other during a remote consultation without any problems, since this does not disrupt the operation of conventional videoconferencing software (which generally does not accept a change of signal format during a videoconference).

The embodiments described herein are given by way of illustration only, and modifications to these embodiments may be made or contemplated while remaining within the scope of the present disclosure. In addition, the various features of these embodiments may be used on their own or be combined with one another. When they are combined, these features may be combined as described above or differently, the scope not being limited to the specific combinations described herein. In particular, unless stated otherwise, a feature described with reference to one embodiment may be applied analogously to another embodiment.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances. Further any standards referenced herein are intended to refer to the standard as published on the priority date of the present application.

The invention claimed is:

1. A patient station enabling transmission of patient data to a remote doctor station, via a telecommunication network, the patient station comprising:
   a processing unit;
   a main display device; and
   at least one first sensor of a first type generating first patient data;
wherein the processing unit is configured to:
   generate a first video signal or a first image from the first patient data and display the first video signal or the first image on the main display device in a first display window;
   capture at least one display area of the first display window to generate a captured video signal;
   generate an output video signal comprising the captured video signal;
   emulate a digital camera peripheral, wherein the output video signal is provided as output from the emulated digital camera peripheral; and
   provide the output video signal to the doctor station via the telecommunication network.

2. The patient station of claim 1, further comprising:
   at least one second sensor of a second type, different from the first type, generating second patient data;
wherein the processing unit is configured to:
   generate a second video signal from the second patient data; and
   generate the output video signal by combining the second video signal and the captured video signal.

3. The patient station of claim 1, wherein the output video signal is provided to the doctor station by way of videoconferencing software executed by the processing unit.

4. The patient station of claim 3, wherein the output video signal is selectable by a user of the patient station from a scrolling menu on a graphical interface of the videoconferencing software.

5. The patient station of claim 1, wherein the processing unit is configured to display the first display window within a second display window of a graphical interface.

6. The patient station of claim 1, wherein the processing unit is configured to automatically redimension the first display window displayed in the graphical interface.

7. The patient station of claim 1, wherein the first display window forms part of a graphical interface dedicated to the first sensor.

8. The patient station of claim 1, wherein the processing unit comprises a main unit and an auxiliary unit, the auxiliary unit being configured to generate the first video signal or the first image from the first patient data and display the first video signal or the first image on an auxiliary display device; and the main unit being configured to duplicate the display of the first video signal or the first image on the main display device in the first display window.

9. The patient station of claim 1, wherein generating the output video signal comprises filtering and/or redimensioning the captured video signal and/or the second video signal.

10. The patient station of claim 1, wherein the processing unit is configured to transmit the output video signal to the doctor station during a remote consultation, and wherein the processing unit is furthermore configured to maintain video parameters of the output video signal fixed, wherein the parameters comprise one or more of a resolution of the output video signal, a frame rate of the output video signal, and a type of digital encoding of the output video signal.

11. The patient station of claim 1, wherein the first sensor comprises one or more of a camera, an echograph, an electrocardiograph, an electroencephalograph, a spirometer, a tensiometer, a thermometer, an oximeter, a scale, a refractor, a tonometer, a pachymeter, a frontofocometer, a keratometer, an autorefractometer, and a radiology apparatus.

12. The patient station of claim 1, further comprising:
   an audio sensor connected to the processing unit and generating a first audio signal,
wherein the processing unit is configured to:
   generate an output audio signal comprising the first audio signal;
   emulate a microphone peripheral, wherein the output audio signal is provided as output from the microphone peripheral; and
   provide the output video signal to the doctor station via the telecommunication network.

13. A method for transmitting patient data to a remote doctor station via a telecommunications network, implemented by a processing unit, the method comprising the following steps:
   generating a first video signal or a first image from first patient data arising from a first sensor of a first type and displaying the first video signal or the first image on a main display device in a first display window;
   capturing at least one display area of the first display window in order to generate a captured video signal;
   generating an output video signal comprising the captured video signal;
   emulating a digital camera peripheral, wherein the output video signal is provided as output from the emulated digital camera peripheral; and
   providing the output video signal to the doctor station via the telecommunication network.

14. The method of claim 13, further comprising:
   generating a second video signal from second patient data arising from a second sensor of a second type; and
   generating the output video signal by combining the second video signal and the captured video signal.

15. The method of claim 13, wherein the output video signal is provided to the doctor station by way of videoconferencing software executed by the processing unit.

16. The method of claim 13, further comprising:
generating a first audio signal from an audio sensor;
generating an output audio signal comprising the first audio signal;
emulating a microphone peripheral, wherein the output audio signal is provided as output from the microphone peripheral; and
providing the output video signal to the doctor station via the telecommunication network.

* * * * *